United States Patent [19]
Gershwin et al.

[11] Patent Number: 6,111,071
[45] Date of Patent: Aug. 29, 2000

[54] RECOMBINANT FUSION PROTEIN COMPRISING PDC-E2, BCOADC-E2 AND OGDC-E2 AND USES THEREOF

[75] Inventors: Eric Gershwin; Patrick S. Leung, both of Davis, Calif.

[73] Assignees: The Regents of the University of California, Oakland, Calif.; Monash University, Victoria, Australia

[21] Appl. No.: 08/881,771

[22] Filed: Jun. 24, 1997

Related U.S. Application Data

[60] Provisional application No. 60/014,719, Jun. 24, 1996.

[51] Int. Cl.[7] .................................................. C07K 14/435
[52] U.S. Cl. .......................... 530/350; 530/403; 435/69.7; 424/185.1; 424/193.1
[58] Field of Search ...................................... 530/350, 395, 530/403; 424/185.1, 93.1; 435/7.1, 69.7

[56] References Cited

PUBLICATIONS

Protein Structures and Molecular Properties, Thomas E. Creighton, Ed. Chapter 7, pp. 265–333, 1984.
Protein Structures and Molecular Properties, Thomas E. Creighton, Ed. Chapter 2, pp. 61–91, 1984.

*Primary Examiner*—Thomas M. Cunningham
*Attorney, Agent, or Firm*—Mandel & Adriano

[57] ABSTRACT

The present invention provides a fusion protein which comprises the E2 subunits of PDC, BCOADC, and OGDC and uses thereof.

5 Claims, 8 Drawing Sheets

SEQ 1 : Amino Acid Residues derived from BCOADC-E2.

GQIVQFKLSD IGEGIREVTV KEWYVKEGDT VSQFDSICEV

QSDKASVTIT SRYDGVIKKL YYNLDDTAYV GKPLVDIETE

ALKDSEEDVV ETPAVSHDEH THQEIKGQKT LGTPAVRR

SEQ2 : Amino Acid Residues derived from PDC-E2.

KNYTLDSSAA PTPQAAPAPT PAATASPPTP SAQAPGSSYP PHMQVLLPAL

SPTMTMGTVQ RWEKKVGEKL SEGDLLAEIE TDKATIGFEV QEEGYLAKIL

VPEGTRDVPL GTPLCIIVEK EADISAFADY RPTEVTDL

SEQ3 : Amino Acid Residues derived from OGDC-E2.

NDVITVQTPA FAESVTEGDV RWEKAVGDAV AEDEVVCEIE TDKTSVQVPS

PANGIIEALL VPDGGKVEGG TPLFTLRKTG AA

FIG. 4

Amino acid sequence of designer molecule.

```
  1  LVPRGSGQIV QFKLSDIGEG IREVTVKEWY VKEGDTVSQF DSICEVQSDK

51  ASVTITSRYD GVIKKLYYNL DDTAYVGKPL VDIETEALKD SEEDVVETPA

101  VSHDEHTHQE IKGQKTLGTP AVRRGSPEFK NYTLDSSAAP TPQAAPAPTP

151  AATASPPTPS AQAPGSSYPP HMQVLLPALS PTMTMGTVQR WEKKVGEKLS

201  EGDLLAEIET DKATIGFEVQ EEGYLAKILV PEGTRDVPLG TPLCIIVEKE

251  ADISAFADYR PTEVTDLEFP GRLERPQNDV ITVQTPAFAE SVTEGDVRWF

301  KAVGDAVAED EVVCEIETDK TSVQVPSPAN GIIEALLVPD GGKVEGGTPL

351  FTLRKTGAAR PAS*L
```

Underlined
AA residue : 7- 124 are derived from BCOADC-E2.

AA residue : 130-267 are derived from PDC-E2.

AA residue : 278-359 are derived from OGDC-E2.

The other aa residues are either derived from or resulted from connecting these lipoyl domains are from plasmid vector pGEX-4T.

* Stop

FIG. 5

Designer nucleotide sequence.

```
   1  ctggttccgc gtggatccGG ACAGATTGTT CAGTTCAAAC TCTCAGACAT
  51  TGGAGAAGGT ATTAGAGAAG TAACTGTTAA AGAATGGTAT GTAAAAGAAG
 101  GAGATACAGT GTCTCAGTTT GATAGCATCT GTGAAGTTCA AAGTGATAAA
 151  GCTTCTGTTA CTATCACTAG TCGTTATGAT GGAGTCATTA AAAAACTGTA
 201  TTATAATCTA GATGATACTG CCTATGTGGG AAAGCCATTA GTAGACATAG
 251  AAACGGAAGC TTTAAAAGAT TCAGAAGAAG ATGTTGTTGA AACCCCTGCT
 301  GTGTCCCATG ATGAACACAC ACACCAAGAG ATAAAGGGCC AGAAAACACT
 351  GGGCACTCCT GCAGTTCGTC GCggatcccc ggaattcAAA AATTATACAC
 401  TGGATTCCTC AGCAGCACCT ACCCCACAAG CGGCCCCAGC ACCAACCCCT
 451  GCTGCCACTG CTTCGCCACC TACACCTTCT GCTCAGGCTC CTGGTAGCTC
 501  ATATCCCCCT CACATGCAGG TACTTCTTCC TGCCCTCTCT CCCACCATGA
 551  CCATGGGCAC AGTTCAGAGA TGGGAAAAAA AAGTGGGTGA GAAGCTAAGT
 601  GAAGGAGACT TACTGGCAGA GATAGAAACT GACAAAGCCA CTATAGGTTT
 651  TGAAGTACAG GAAGAAGGTT ATCTGGCAAA AATCCTGGTC CCTGAAGGCA
 701  CAAGAGATGT CCCTCTAGGA ACCCCACTCT GTATCATTGT AGAAAAAGAG
 751  GCAGATATAT CAGCATTTGC TGACTATAGG CCAACCGAAG TAACAGATTT
 801  Agaattcccg ggtcgactcg agcggccgcA GAATGATGTG ATTACAGTCC
 851  AGACCCCAGC GTTTGCAGAG TCTGTCACAG AGGGAGATGT CAGGTGGGAG
 901  AAAGCTGTTG GAGATGCAGT TGCAGAAGAT GAAGTGGTGT GTGAGATTGA
 951  GACAGACAAG ACTTCTGTGC AGGTTCCATC ACCAGCAAAT GGCATCATTG
1001  AAGCTCTTTT GGTACCCGAT GGGGGCAAAG TTGAAGGAGG AACTCCTCTA
1051  TTCACACTCA GGAAAACCGG TGCTGCgcgg ccggcatcgt gactga
```

Bases derived from BCOADC-E2 :  18-372. (GGACA-----CGTCGC)
Bases derived from PDC-E2 :     388-801. (AAAAA-----ATTTA)
Bases derived from OGDC-E2 :    830-1076 (AGAAT----GCTGC)

Bases derived from plasmid vector pGEX-4T or resulted from cloning of the inserts are shown in small letters.
Bases derived from the inserts are in capital letters.

FIG. 6

NUCLEOTIDE SEQUENCE OF HYBRID MOLECULE EXPRESSING THE
LIPOYL DOMAINS OF BCOADC-E2, PDC-E2 AND OGDC-E2 IN TANDEM.

NUCLEOTIDE SEQUENCE OF BCOADC-E2 AMINO ACID RESIDUES 1-118
LINKED TO BAM HI (GGATCC) SITE

5'- GGATCC-

GGACAGATTG TTCAGTTCAA ACTCTCAGAC ATTGGAGAAG GTATTAGAGA

AGTAACTGTT AAAGAATGGT ATGTAAAAGA AGGAGATACA GTGTCTCAGT

TTGATAGCAT CTGTGAAGTT CAAAGTGATA AAGCTTCTGT TACTATCACT

AGTCGTTATG ATGGAGTCAT TAAAAAACTG TATTATAATC TAGATGATAC

TGCCTATGTG GGAAAGCCAT TAGTAGACAT AGAAACGGAA GCTTTAAAAG

ATTCAGAAGA AGATGTTGTT GAAACCCCTG CTGTGTCCCA TGATGAACAC

ACACACCAAG AGATAAAGGG CCAGAAAACA CTGGGCACTC CTGCAGTTCG

TCGC-GGATCC-3'

NUCLEOTIDE SEQUENCE OF PDC-E2 AMINO ACID RESIDUE 91-228 LINKED
TO ECOR I (GAATTC) SITE

5'-GAATTC-

AAAAATTATA CACTGGATTC CTCAGCAGCA CCTACCCCAC AAGCGGCCCC

AGCACCAACC CCTGCTGCCA CTGCTTCGCC ACCTACACCT TCTGCTCAGG

CTCCTGGTAG CTCATATCCC CCTCACATGC AGGTACTTCT TCCTGCCCTC

TCTCCCACCA TGACCATGGG CACAGTTCAG AGATGGGAAA AAAAAGTGGG

TGAGAAGCTA AGTGAAGGAG ACTTACTGGC AGAGATAGAA ACTGACAAAG

CCACTATAGG TTTTGAAGTA CAGGAAGAAG GTTATCTGGC AAAAATCCTG

GTCCCTGAAG GCACAAGAGA TGTCCCTCTA GGAACCCCAC TCTGTATCAT

TGTAGAAAAA GAGGCAGATA TATCAGCATT TGCTGACTAT AGGCCAACCG

AAGTAACAGA TTTA - GAATTC-3'

FIG. 7A

NUCLEOTIDE SEQUENCE OF RAT OGDC-E2 AMINO ACID RESIDUE 67-147 LINKED TO NOT I (GCGGCCGC) SITE.

5'-GCGGCCGC

AGAATGATGT GATTACAGTC CAGACCCCAG CGTTTGCAGA GTCTGTCACA

GAGGGAGATG TCAGGTGGGA GAAAGCTGTT GGAGATGCAG TTGCAGAAGA

TGAAGTGGTG TGTGAGATTG AGACAGACAA GACTTCTGTG CAGGTTCCAT

CACCAGCAAA TGGCATCATT GAAGCTCTTT TGGTACCCGA TGGGGGCAAA

GTTGAAGGAG GAACTCCTCT ATTCACACTC AGGAAAACCG GTGCTGC-

GCGGCCGC- 3'

FIG. 7B

RECOMBINANT FUSION PROTEIN COMPRISING PDC-E2, BCOADC-E2 AND OGDC-E2 AND USES THEREOF

This application is based on a provisional application, U.S. Ser. No. 60/014,719, filed Jun. 24, 1996.

Throughout this application various publications are referenced. The disclosures of these publications in their entireties are hereby incorporated by reference into this application in order to more fully describe the state of the art to which this invention pertains.

BACKGROUND OF THE INVENTION

Primary biliary cirrhosis (PBC) is a well-characterized autoimmune liver disease that results in the destruction of intrahepatic bile ducts with progressive inflammatory scarring (Kaplan M. M., Adv Intern Med 32:359–377, 1987). The disease is marked by an autoantibody response to mitochondria, originally identified using immunofluorescence (Berg, P. A. et al., 20 Hepatology 2:123–131, 1986; Frazer, I. H. et al., J. Immunol 135:1739–1745, 1985; Kenna, J. G. et al., J. Immunol. Methods 73:401–413, 1984; Kaplan, M. M. et al, Hepatology 4: 727–730, 1984; Walker, J. G. et al., Lancet 1:827–831, 1965).

A characteristic serologic feature observed in sera from patients with PBC is the presence of high titers of antibodies directed against mitochondrial antigens (AMA) (Mackay I. R., N Engl J Med 1958; 258:185–187; Walker, J. G. et al., Lancet 1965; 1:827–831; Berg, P. A. et al., J Exp Med 1967; 126:277–290; Gershwin M E and Mackay I R. Gastroenterology 1991; 100: 822–833). The major autoantigens recognized by sera from PBC patients have been identified as members of the 2-oxo-acid dehydrogenase complex (2-OADC) family, including the E2 subunit of the pyruvate dehydrogenase complex (PDC-E2), the E2 subunit of the branched chain 2-oxo-acid dehydrogenase complex (BCOADC-E2), the E2 subunit of the 2-oxo glutarate dehydrogenase complex (OGDC-E2), E1" subunits of PDC and protein X (Yeaman, S. J. et al., Lancet 1988; 1:1067–1070; Van de Water J, et al., J Exp Med 1988; 167:1791–1799; Fussey S P M, et al., Proc Natl Acad Sci USA 1988;85:8654–8658; Fregeau D R, et al., J Immunol 1989;142;3815–3820; Surh C D, et al., Hepatology 1989;10:127–133; Fregeau D R, et al., J Immunol 1990;144:1671–1676; Fregeau D R, et al., Hepatology 1990; 1 1:975–981).

Among these enzyme components, the E2 component of PDC, or dihydrolipoamide dehydrogenase, is the major autoantigen of PBC since the serum samples of the majority of patients (80 to 90%) contain PDC-E2 specific AMA. In addition to PDC-E2, approximately 60% of patients with PBC are also reactive with BCOADC-E2 (Mutimer D J, et al., Hepatology 1989;10:403–407; Leung P S C, et al., Hepatology 1992;15:367–372). Interestingly, 4% to 13% of sera from patients with PBC recognize only the BCOADC-E2 but not the PDC-E2 (Leung P S C, et al., Hepatology 1992;15:367–372; Van de Water J, et al., N Engl J Med 1989;320:1377–1380; Iwayama T, et al., Int Arch Allergy Immunol 1992;99:28–33). The E2 component of OGDC-E2, dihydrolipoamide succinyltransferase, is recognized in 30% to 80% of sera from patients with PBC (Fregeau D R, et al., Hepatology 1990; 1 1:975–981; Mutimer D J, et al., Hepatology 1989;10:403–407; Leung P S C, et al., Inflammatory hepatobiliary cirrhosis. pp. 1429–1443. 1996. In: Clin. Immunology. Principles and Practice. Rich. R. R.(Ed). Mosby. Year book. Inc. St. Louis, Mo., USA). The immunodominant epitopes of PDC-E2 and BCOADC-E2 have been previously mapped to their lipoic acid binding domains (Surh C D, et al., J Immunol 1990;144:3367–3374; Leung P S C, et al., Hepatology 1995; 22:505–513). Although PDC-E2 contains two lipoic acid binding domains, the reactivity of AMA is about 100 times stronger to the inner lipoyl domain (Van de Water J, et al., J Exp Med 1988; 167:1791–1799; Surh C D, et al., Hepatology 1989;10:127–133).

The complementary DNA (cDNA) of PDC-E2, BCOADC-E2 and PDC-E1" have been isolated and used to produce recombinant proteins designated PDC-E2, BCOADC-E2, and PDC-E1", respectively. A strong reactivity of patient AMA to these proteins by immunoblotting and enzyme-linked immunosorbent assays (ELISA) was demonstrated (Leung P S C, et al., Hepatology 1992;15:367–372; Van de Water J, et al., N Engl J Med 1989;320:1377–1380; Gershwin M E, et al., J Immunol 1987;138:3525–353 1; Coppel R L, et al., Proc Natl Acad Sci USA 1988; 85:7317–7321; Griffin T A, et al., J Biol Chem 1988;263:14008–14014; Danner DJ, et al., J Biol Chem 1989;264:7742–7746; Ho L, et al., Proc Natl Acad Sci USA 1989;86:5330–5334; Surh C D, et al., Hepatology 1989;9:63–68; Iwayama T, et al., J Autoimmunity 1991 ;4:769–778).

SUMMARY OF THE INVENTION

The present invention provides a recombinant fusion protein comprising PDC-E2, BCOADC-E2, and OGDC-E2. Further, the invention provides a clone, designated pML-MIT3, that coexpresses the immunodominant epitopes within the three distinct lipoyl domains. The present invention provides the basis for an extremely sensitive and specific diagnostic ELISA for AMA in PBC subjects.

BRIEF DESCRIPTION OF THE FIGURES

FIG. 4 provides the amino acid sequence of the lipoyl domains and flanking regions of BCOADC-E2 (SEQ ID NO: 1), PDC-E2 (SEQ ID NO: 2), and OGDC-E2 (SEQ ID NO: 3) used in construction of pML-MIT3.

FIG. 5 provides the amino acid sequence (SEQ ID NO: 4) of one embodiment of the recombinant fusion protein.

FIG. 6 provides the complete nucleic acid sequence (SEQ ID NO: 5) of lipoyl domains and flanking regions of PDC-E2, BCOADC-E2, and OGDC-E2 for the vector pML-MIT3. Bases derived from plasmid vector pGEX-4T or resulted from cloning of the inserts are shown in lower capital letters (e.g., linkers). Bases derived from the inserts (i.e., BCOADC, PDC, and OGDC) are in capital letters.

FIG. 7 provides the nucleotide sequence of BCOADC-E2 (SEQ ID NO: 7), PDC-D2 (SEQ ID NO: 8), and OGDC-E2 (SEQ ID NO: 9).

DETAILED DESCRIPTION OF THE INVENTION

Definitions

Figure 1:
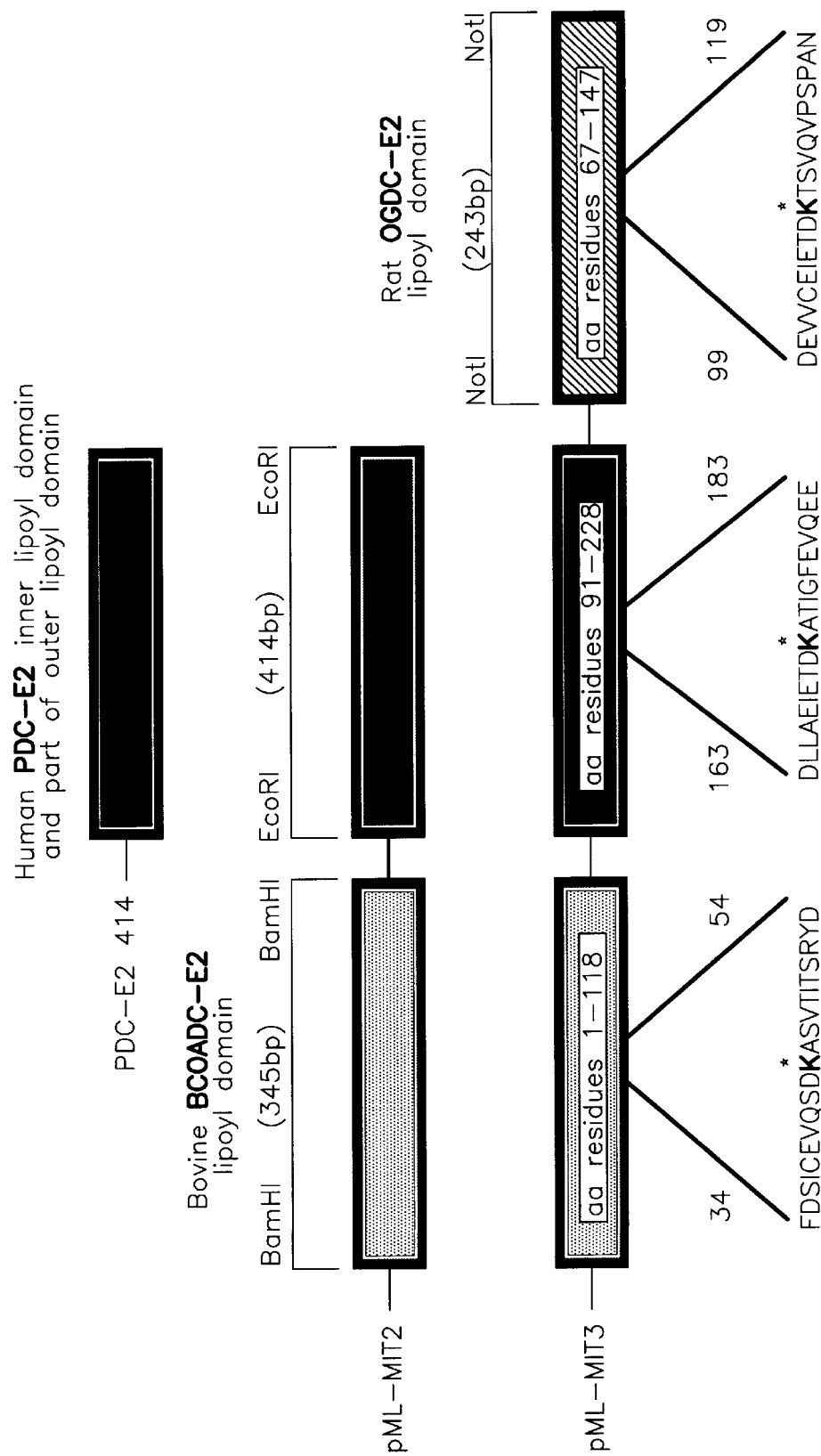
FIG. 1 is a diagrammatic representation of PDC-E2 (414 bp), (SEQ ID NO. 2) pML-MIT2 and pML–MIT3. PDC-E2 (414 bp) contains the human PDC-E2 inner lipoyl domain and part of the outer lipoyl domain. pML-MIT2 contains the bovine BCOADC-E2 lipoyl domain and PDC-E2 (414 bp). pML-MIT3 consists of lipoyl domains of PDC-E2, BCOADC-E2 and OGDC-E2. The number of base pairs and amino acid residues of each of the lipoyl domain are shown. An asterisk indicates the lysine residues where the lipoic acid is bound.
Figure 2A:
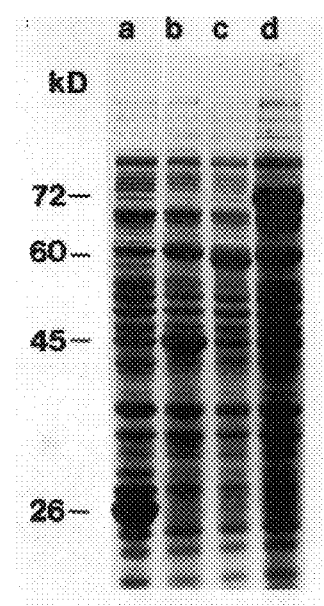
FIG. 2 is a photograph showing results of SDS-PAGE and inmmunoreactivity of PBC sera against recombinant fusion proteins. 2A represents a Coomassie Brilliant Blue R-250 stain of IPTG induced E. coli expression clones of pGEX4T-1 (control, lane a), PDC-E2 (lane b), pML-MIT-2 (lane c) and pML-MIT-3 (lane d). Please note the presence of a recombinant fusion protein of 26 kD of GSH in lane a; 45 kD of recombinant PDC-E2 in lane b; 60 kD of pML-MIT-2 in lane c; and 72 kD of pML-MIT-3 in lane d. In 2B, 2C and 2D, three different PBC sera with known reactivity against PDC-E2 only (2B), BCOADC-E2 only (2C) and OGDC-E2 only (2D) were probed against blots of the SDS-PAGE separated proteins. It should be noted that the sera with PDC-E2 reactivity only (2B) recognized the 45 kD band of PDC-E2, the 60 kD band in pML-MIT-2 and the 72 kD band in pML-MIT-3 (2B, lanes b-d). PBC sera with BCOADC-E2 reactivity only (2C) recognized the 60 kD band in pML-MIT-2 and the 72 kD band in pML-MIT-3 but not the PDC-E2 band (2C, lanes b-d). Likewise, sera with OGDC-E2 reactivity only (2D) recognized only the 72 kD band in pML-MIT-3 (lane d) but not other bands (2D lanes a-c). Reactivities to low molecular weight bands in 2B, 2C and 2D are due to degraded recombinant proteins.
Figure 2B:
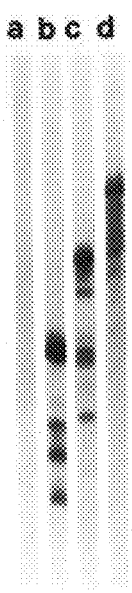
Figure 2C:
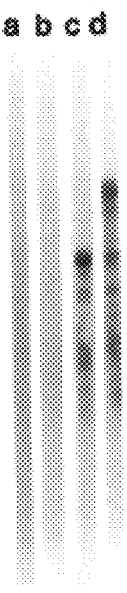
Figure 2D:
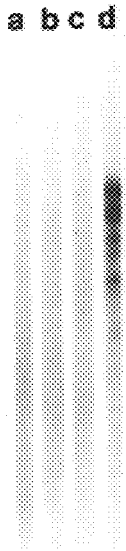
Figure 3A:
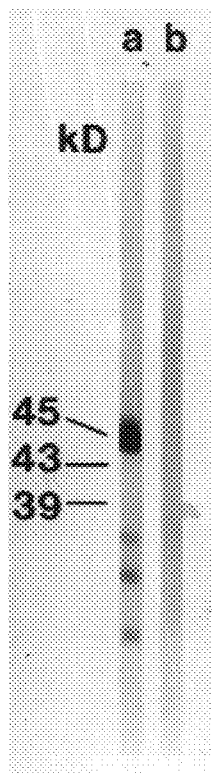
FIG. 3 is a photograph showing specific inhibition of AMA reactivity by recombinant fusion protein molecule. Recombinant proteins of PDC-E2 (3A), BCOADC-E2 (3B) and OGDC-E2 (3C) inner lipoyl domains were resolved by SDS-PAGE, transferred onto nitrocellulose filters and probed with a 1: 1,000 dilution of sera from patients with PBC. AMA reactivities were directed against recombinant proteins of PDC-E2, BCOADC-E2 and OGDC-E2 at 45 kD (3A, lane a), 43 kD (3B, lane a) and 39 kD (3C, lane a) respectively. These specific reactivities on immunoblots were removed when the sera were first incubated with recombinant pML-MIT-3 as shown in lane b of FIGS. 3A, 3B and 3C. Similarly, when PBC sera were probed against preparations of beef heart mitochondria (3D, lane a), absorption of sera with recombinant pML-MIT-3 (3D, lane b) removed the reactivities to the 74 kD PDC-E2, 52 kD BCOADC-E2 and 48 kD OGDC-E2 proteins but not to the 41 kD PDC E1" band.
Figure 3B:
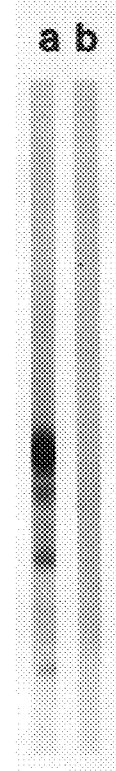
Figure 3C:
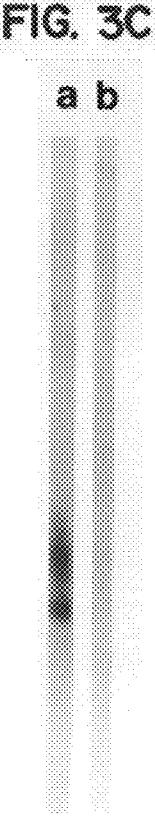
Figure 3D:
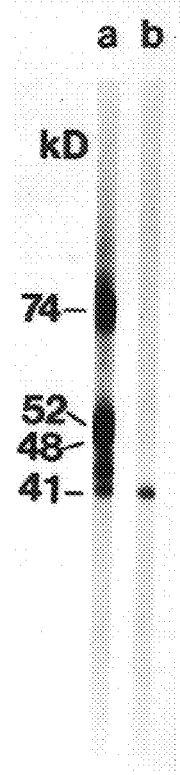

As used in this application, the following words or phrases have the meanings specified.

As used herein "PDC-E2" means the E2 subunit of the pyruvate dehydrogenase complex. This includes the entire E2 subunit or any portion thereof which is recognized and bound by an antimitochondrial antibody. Examples of such antibodies are well known in the art. Murine monoclonal antibodies to the mitochondrial autoantigen PDC-E2 were isolated (Surh, et al., J. Inmmunol. 1990; 144: 3367–3374). Recently, Cha et al. isolated and characterized a human antibody specific to PDC-E2. (Cha, et al., Proc. Natl. Acad. Sci. USA, 1993; 90: 2527–2531). These antibodies are readily available to be used to identify a mitochondrial antigen.

As used herein "BCOADC-E2" means the E2 subunit of the branched chain 2-oxo-acid dehydrogenase complex. This includes the entire E2 subunit or any portion thereof which is recognized and bound by an antimitochondrial antibody. Examples of such antibodies are well known (Fregeau, et al. (1989) J. Immunol. 142:3815–3820; Surh et al. (1989) Hepatology 9:63–68).

As used herein "OGDC-E2" means the E2 subunit of the 2-oxo glutarate dehydrogenase complex. This includes the entire E2 subunit or any portion thereof which is recognized and bound by an antimitochondrial antibody. Examples of such antibodies are well known (Fregeau et al. (1990) Hepatology 11:975).

In order that the invention herein described may be more fully understood, the following description is set forth.

Fusion Protein Molecules of the Invention

The present invention provides a recombinant fusion protein comprising PDC-E2, BCOADC-E2, and OGDC-E2. In accordance with the practice of the invention, the particular order of PDC-E2, BCOADC-E2, and OGDC-E2 in the fusion protein is not critical. Varying the location of the three E2 subunits anywhere in the fusion protein is included within the scope of the invention. In one preferred embodiment, the recombinant fusion protein comprises BCOADC-E2, PDC-E2, and OGDC-E2 in that order (SEQ ID NO 4).

In one embodiment of the invention, PDC-E2 is that portion having the lipoic acid binding domain of the PDC. BCOADC-E2 is that portion having the lipoic acid binding domain of the branched chain BCOADC. OGDC-E2 is that portion having the lipoic acid binding domain of OGDC.

Amino Acid Sequences Encoding Molecules of the Invention

The invention also provides an amino acid sequence encoding one embodiment of a recombinant fusion protein of the invention. The sequence is shown in FIG. 4.

Additionally, in one embodiment, the portion of the lipoic acid binding domain of PDC comprises an amino acid sequence beginning with lysine at amino acid position 1 to leucine at amino acid position 138 of SEQ ID NO 2.

Also, the portion of the lipoic acid binding domain of BCOADC can comprise an amino acid sequence beginning with glycine at amino acid position 1 to arginine at amino acid position 118 SEQ ID NO 1.

The portion of the lipoic acid binding domain of OGDC comprises an amino acid sequence beginning with asparagine at amino acid position 1 to alanine at amino acid position 82 SEQ ID NO 3.

Amino acid molecules encoding the molecules of the invention can be modified, i.e., by amino acid substitutions within the molecule, so as to produce derivative molecules thereof. Such derivative molecules would retain the functional property of the recombinant fusion protein molecules of the invention, namely, it would bind anti-mitochondrial antibodies in order to detect its presence.

These amino acid substitutions include, but are not necessarily limited to, amino acid substitutions known in the art as "conservative". Additionally, these substitutions include making changes in the amino acid sequence, such changes resulting in allelic variants of the fusion protein molecules of the invention from any mammal, e.g., PCD-E2, BCOADC-E2, and OGDC-E2 from any of rat, mouse, pig, primate, or human. The fusion protein molecules include hybrid molecules, i.e., having components from various species, Hybrid molecules include components from any of rat, mouse, pig, primate, and/or human, in a single fusion protein.

Additionally, amino acid changes can be effected by chemical alteration of the amino acid sequence.

In accordance with the practice of the invention, the flanking domains and the interdomain regions within the fusion protein can be freely changed or mutated. The only limitation is that the changes must not hinder the components, PDC-E2, BCOADC-E2, and OGDC-E2, from being recognized and bound by antibody.

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa.

Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Nucleic Acid Sequences Encoding Molecules of the Invention

The invention also provides nucleic acid molecules encoding the molecules of the invention. The nucleic acid molecule can be deoxyribonucleic acid (DNA) or ribonucleic acid (RNA) or hybrids thereof.

In one embodiment, the fusion protein of the invention is encoded by the nucleic acid sequence shown in FIG. 6 (SEQ ID NO 5).

As to the components of the fusion protein of the invention, in one embodiment, PDC-E2 is encoded by the nucleic acid sequence shown in FIG. 7 (SEQ ID NO 8). Additionally, in one embodiment, BCOADC-E2 is encoded by the nucleic acid sequence shown in FIG. 7 (SEQ ID NO 7). Further, in one embodiment, OGDC-E2 is encoded by the nucleic acid sequence shown in FIG. 7 (SEQ ID NO 6).

Methods for Making the Molecules of the Invention

Vectors encoding fusion proteins are encompassed by the present invention. In one embodiment, the expression vector encodes a recombinant DNA molecule encoding the fusion protein of the invention. The recombinant DNA molecule can comprise a nucleotide sequence operatively linked to an expression control sequence.

The invention also provides a host vector system comprising the expression vector transfected into a compatible host cell. Examples of compatible eucaryotic host cells include a yeast cell, a plant cell, or an animal cell.

The method also provides a method of producing a protein. This method comprises growing the host vector system so as to produce the protein in the host and recovering the protein so produced.

Vectors for use in the methods of the present invention include but are not limited to viral vectors including adenoviruses, retroviral vectors, or adeno-associated viral (AAV) vectors.

Retroviral vectors and adenoviruses offer an efficient, useful, and presently the best-characterized means of introducing and expressing foreign genes efficiently in mammalian cells. These vectors have very broad host and cell type ranges and express genes stably and efficiently.

Other virus vectors that may be used such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles. For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences (Kaufinan R. J.; Identification of the component necessary for adenovirus translational control and their utilization in cDNA expression vectors. *PNAS USA*, 1985 82:689).

Retroviruses are packages designed to insert viral genes into host cells (Guild B, et al., Development of retrovirus vectors useful for expressing genes in cultured murine embryonic cells and hematopoietic cells in vivo. *J Virol* 1988; 62:795; Hock R A, et al., Retrovirus mediated transfer and expression of drug resistance genes in human hemopoietic progenitor cells. *Nature* 1986; 320:275).

The basic retrovirus consists of two identical strands of RNA packaged in a proviral protein. The core surrounded by a protective coat called the envelope, which is derived from the membrane of the previous host but modified with glycoproteins contributed by the virus.

Methods for Using the Molecules of the Invention

The invention also provides a method for detecting an anti-mitochondrial antibody in a sample from a subject, detection of the antibody being indicative of an auto-immune liver disease. This method comprises the steps of contacting the sample with the fusion protein under conditions such that the fusion protein binds to the antimitochondrial antibody, thereby forming a fusion protein/antibody complex; and detecting the presence of the complex which is indicative of an auto-immune liver disease.

In accordance with the practice of the invention, the sample can be a serum sample. The sample can be immobilized. The method of detection can be by ELISA. Alternatively, the method of detection can be effected by immunoblotting.

The subject can be an animal subject. Alternatively, the subject can be a human subject.

Advantages of the Invention

This invention involves a recombinant fusion protein having three immunodominant lipoyl domains of PDC-E2, BCOADC-E2 and OGDC-E2. A total of 321 sera including 186 sera from patients with PBC to test the immunoreactivity of pMIT3, was examined. Out of 186 sera from patients with PBC, 152 sera (81.7%) reacted with recombinant fusion protein of PDC-E2 whereas 171 sera (91.9%) showed positive reactivities when probed by immunoblotting against the recombinant fusion protein expressed from the pML-MIT3 clone. Out of 34 PBC sera which did not react with recombinant PDC-E2, 18 sera contained BCOADC-E2 specific AMA and one serum possessed only OGDC-E2 specific AMA.

An ELISA, using affinity purified recombinant fusion protein of pML-MIT3 clone as the antigen source, was developed to quantify specific AMAs in patients with PBC. None of the 135 control sera from patients with primary sclerosing cholangitis, chronic autoimmune hepatitis, systemic lupus erythematosus or healthy volunteers showed significant reactivity against pML-MIT3 recombinant fusion protein in the ELISA assay. Our results indicate that an ELISA using recombinant, cloned autoantigen of pML-MIT3 is a powerful and very specific method for the detection of AMA. It is thus possible to develop a simple, accurate, rapid and sensitive ELISA for the detection of AMA specific to PBC.

By enzyme-linked immunosorbent assay (ELISA), more than 95% of patients with PBC have been clinically found to have such anti-mitochondrial antibodies (Frazer, I. H., et al., J. Immunol 135:1739–1745, 1985; Lindenborn, et al., Hepatology 5:763–769, 1985). Therefore, detection of anti-mitochondrial autoantibodies (AMA) becomes critical in the diagnosis of primary biliary cirrhosis (PBC).

Conventional laboratory assays to detect AMA are dependent on the time consuming method of immunofluorescence microscopy, a method often plagued by problems of non-specificity. When crude mitochondrial antigen preparations are used, subjects with a variety of diseases, including patients with liver diseases other than PBC, certain connective tissue diseases, drug reactions, and occasionally even healthy individuals, tested positive for antibodies against mitochondria Compared with other methods such as RIA, immunofluorescence microscopy, passive hemagglutination and immunoblotting, the use of a recombinant fusion molecule of the invention offers a more rapid, simple and specific method for the detection of AMA.

The sensitivity of the ELISA assay using the hybrid molecules of the invention was equal to that obtained by immunoblotting. There have been previous reports on use of a dual-headed molecule containing the bovine BCOADC-E2 and rat OGDC-E2 reactive epitopes (Leung P S C, et al., Hepatology 1992;15:367–372). However, this molecule does not contain the OGDC-E2 reactive epitope.

The present invention is more useful than the dual headed molecule in that it can detect antibodies to all three lipoyl domains of the E2 components of 2-OADC with higher sensitivity.

AMA from PBC patients recognize mammalian mitochondrial proteins from various species including mouse, rat, bovine and human with similar affinities. Thus, it is unlikely that there will be significant differences in detection sensitivity and specificities if only human cDNA fragments are used in the construction of the hybrid expression system. In particular it should be stressed that the molecule of the invention has a higher sensitivity in diagnostic testing than use of PDC-E2 alone. The conventional use of irmmunofluorescence microscopy for the detection of AMA can be replaced by assays based on the fusion protein of the present invention. In addition, the fusion protein can be used in immunotherapy, e.g., production of vaccine, etc.

EXAMPLE 1

Materials and Methods

Subjects

Sera were collected from 186 patients with a documented clinical and laboratory diagnosis of PBC from the serum banks of the Mayo Clinic (Rochester, Minn.) and the University of California (Davis, Calif.) (Kaplan M M. Adv Intern Med 1987;32:359–377; Williamson J M, et al., J Clin Pathol 1985;38:1007–1012). In addition, sera from 22 patients with primary sclerosing cholangitis (PSC), 15 patients with chronic autoimmune hepatitis (CAH), 34 patients with systemic lupus erythematosus (SLE) and 64 normal subjects were used as controls.

Construction of the Hybrid Clone

The AMA reactive epitopes of human PDC-E2, bovine BCOADC-E2 and rat OGDC-E2 were cloned and expressed in the plasmid vector pGEX-4T-1 (Pharmacia, Alameda, Calif.) (FIG. 1). Briefly, a 414 bp EcoRI fragment coding for the PDC-E2 inner lipoyl domain and part of the outer lipoyl domain, amino acid residues 91 to 228 of the mature PDC-E2, was amplified by the polymerase chain reaction (PCR) with the following synthetic oligonucleotide primers: primer 1; 5'-GGA ATT CAA AAA TTA TAC ACT G-3' (SEQ ID NO 9) [nucleotide position 1065 to 1079 in the cDNA for the human PDC-E2 (Coppel R L, et al., Proc Natl Acad Sci USA 1988; 85:7317–7321)] and primer 2; 5'-GGA ATT CTA AAT CTG TTA CTT C-3' (SEQ ID NO 10) (nucleotide position 1478 to 1464 in the same full length CDNA as above) (Coppel R L, et al., Proc Natl Acad Sci USA 1988; 85:7317–7321).

The amplified PCR product was digested with restriction endonuclease EcoRI and purified by agarose gel electrophoresis followed by phenol and ether extraction. The purified cDNA fragments obtained from the digestion of the PCR product were then ligated into the EcoRI site of pGEX-4T-1 and transformed into *E. coli* DH5α for expression as previously described (Leung P S C, et al., Hepatology 1990; 12:1321–1328). Transformants were then plated onto nitrocellulose filters on Luria-Bertani medium agar plates containing 25 µg/ml ampicillin (LB-Ampicillin plate) and tested for expression of recombinant PDC-E2 by colony immunoassay (Leung P S C, et al., Hepatology 1995; 22:505–513; Kemp D J, et al., Proc Natl Acad Sci USA 1983;80:3787–3791).

To induce recombinant fusion protein the colonies were replica plated onto nitrocellulose filters and induced with 10 mM IPTG (isopropyl-β-thio-galacto pyranoside) for four hours. Thereafter, the colonies were lysed in 1% sodium dodecyl sulfate (SDS)/chloroform for 20 minutes. After removing the lysed colonies, the nitrocellulose filters were blocked in 3% milk in phosphate-buffered saline (PBS), pH 7.4 and then incubated for 2 hours with 1:200 diluted pooled sera from several different PBC patients, which were previously shown to be positive for the 74 kD mitochondrial antigen when probed against beef heart mitochondrial preparation in immunoblotting. After three 10-minute washes in PBS/0.05% Tween 20, the bound antibodies were detected by $^{125}$I-labeled anti-human immunoglobulin (Ig) (Amersham, Arlington, EL) diluted at 1:1,000 in PBS containing 3% milk.

After washing as before, nitrocellulose filters were exposed to X-ray film overnight. The presence of the cDNA inserts were determined by both DNA-hybridization using $^{32}$P-labeled human PDC-E2 cDNA fragment as probe and plasmid DNA analysis on 1% agarose gel electrophoresis (Leung P S C, et al., Hepatology 1990; 12:1321–1328; Leung P S C and Gershwin M E. Immunomethods 1992; 1:149–157). The recombinant plasmid expressing the immunodominant epitopes of PDC-E2 was designated as PDC-E2 (414 bp).

The BCOADC-E2 epitope (amino acid residues 1 to 118) was amplified, cloned into the BamHI site of pGEX-4T-1 using primer pairs 5'-CGC GGA TCC GGA CAG ATT GTT CAG TTC-3'(SEQ ID NO 11) and 5'-CGC GGA TCC GCG ACG AAC TGC AGG AGT-3'(SEQ ID NO 12) as forward and reverse primers pairs respectively. Likewise, the OGDC-E2 epitope (amino acid residues 67 to 147) was amplified using primer pairs 5'-AAG GAA AAA AGC GGC CGC ATA ATG ATG TGA TTA C-3'(SEQ ID NO 13) and 5'-AAG GAA AAA AGC GGC CGC TCA GCA CCG GTT TTC C-3'(SEQ ID NO 14) as forward and reverse pairs respectively and cloned into the NotI site of pGEX-4T-1 (Griffin TA, et al., J Biol Chem 1988;263:14008–14014; Nakano K, et al., J Biol Chem 199 1;266:19013–19017). Successful cloning and expression of BCOADC-E2 and OGDC-E2 were confirmed by DNA hybridization and immunoassay with rabbit anti-BCOADC-E2 antibodies and affinity purified PBC patient serum against recombinant OGDC-E2 respectively (Griffin T A, et al., J Biol Chem 1990;265:12104–12110; Griffin T A and Chuang D T., J Biol Chem 1990;265:13174–13180).

The recombinant plasmid coexpressing additional immunodominant epitopes of PDC-E2 and BCOADC-E2 was designated as pML-MIT2 and a positive clone coexpressing the immunodominant epitope of OGDC-E2 was designated pML-MIT3. The presence of two distinct immunoreactive proteins expressed by hybrid clone pML-MIT2 and three by pML-MIT3 were reconfirmed by immunoblotting using three different PBC patients sera with antibodies to the 74 kD PDC-E2, 52 kD BCOADC-E2 and 48 kD OGDC-E2 respectively. The nucleotide sequence for pML-MIT2 is shown in FIG. 6. pML-MIT2 comprises the sequence derived from BCOADC-E2 (nucleotide positions 18–372) and PDC-32 (nucleotide positions 388–801). Bases derived from the plasmid vector pGEX-4T or resulted from cloning of the inserts (i.e., linkers).

Additionally, a BamHI cDNA fragment coding for lipoyl domain of bovine BCOADC-E2 was cloned and expressed in pGEX4T. This clone was designated as BCOADC-E2 118. Furthermore, OGDC-E2 was expressed from the CDNA clone for the lipoyl domain of rat OGDC-E2, amino acid residues 67 to 147 of the mature protein. The positive clone for rat OGDC-E2 used in this study was designated OGDC-E2 (243 bp). These two clones for BCOADC-E2 and OGDC-E2 were tested for reactivity by immunoblotting as described below.

SDS-PAGE and Immunoblotting

The expressed fusion proteins from PDC-E2 (414 bp), pML-MIT2 and pML-MIT3 were verified by sodium dodecyl sulfate polyacrylamide gel electrophoresis (SDS-PAGE) and immunoblotting analysis. SDS-PAGE was performed on 1.5 mm-thick slab gels with a 4.75% stacking gel and a 10% separating gel (Laemmli U K., Nature 1970;227:680–685). Briefly, an overnight culture of transformed $E.$ $coli$ was diluted 1 :10 in 4 ml of LB medium containing 25 $\mu$/ml ampicillin and grown for one hour at 37EC; IPTG was added to a final concentration of 1 mM for the induction of recombinant protein expression. Four hours later, 1 ml of cells were pelleted and resuspended in 200 $\mu$l of sample buffer (125 mM Tris-HCI, pH 6.8, containing 4% SDS, 20% glycerol and 5% 2-mercaptoethanol) then boiled for 5 minutes, and resolved on SDS-PAGE.

Bovine heart mitochondria (BHM) were prepared as previously described (Schneider W C and Hogeboom G H., J Biol Chem 1950; 183; 123–128). Gels were run at 30 mA constant current at room temperature. Separated proteins were either stained for protein with Coomassie Brilliant Blue R or transferred electrophoretically to nitrocellulose filters (Micron Separations Inc., Westboro, Mass.) as described (Towbin H, et al., Proc Natl Acad Sci 1979;76:4350–4354). After transfer, nitrocellulose filters were blocked in 3% milk powder in PBS, pH 7.4 at room temperature for 30–60 minutes and then probed for 1 hour with appropriate sera diluted at 1:1000 for PBC patients and 1:500 for control group patients in 3% milk powder in PBS, pH 7.4. After three 1 0-minute washes with PBS/0.05% Tween, the strips were incubated for an additional hour with 0.1 $\mu$Ci per ml $^{125}$I-labeled sheep anti-human immunoglobulin (Amersham, Arlington, Ill.). The strips were then washed as before and exposed to X-ray film overnight.

Specificity of Hybrid Molecules Expressed from pML-MIT2 and pML-MIT3 Clones

To demonstrate that pML-MIT2 and pML-MIT3 expressed recombinant fusion proteins which reacted only with PBC patient sera, $E.$ $coli$ lysates of the expressing clone, including the PDC-E2 (414 bp) clone, they were probed by immunoblotting with 1:1000 dilution sera from PBC patients and normal volunteers as well as patients with PSC and CAH.

Absorption of PBC sera with PML-MIT3 Fusion Protein

To further verify that the fusion protein produced by pML-MIT3 contains PDC-E2, BCOADC-E2 and OGDC-E2 reactive epitopes recognized by PBC sera, PBC sera diluted at 1:1000 were extensively absorbed with 10 mg/ml of $E.$ $coli$ lysates from pML-MIT3 and wild type pGEX-4T-1 clone overnight at 4EC. The absorption mixtures were centrifuged at 14,000 rpm and the supernatant sera were then tested for reactivity against beef heart mitochondrial preparation as well as recombinant PDC-E2 (414 bp), BCOADC-E2 (118 bp) and OGDC-E2 (243 bp) proteins by immunoblotting as described above.

Preparation of Recombinant Fusion Proteins

Two different recombinant fusion proteins used in ELISA were prepared as described previously (Van de Water J, et al., N Engl J Med 1989;320:1377–1380). The recombinant peptide containing the entire inner lipoyl domain and part of the outer lipoyl domain, encompassing amino acid residues 91 to 228 of the mature PDC-E2 molecule, was expressed from a cDNA clone of PDC-E2 (414 bp). Likewise, the recombinant hybrid molecule was produced by pML-MIT3 clones. The PDC-E2 (414 bp) and pML-MIT3 expressing recombinant peptides that are fused to glutathione-Transferase have a total molecular weight of 45 kD and 72 kD respectively. Overnight cultures of $E.$ $coli$ expression clones of recombinant PDC-E2 (414 bp) and pML-MIT3 were diluted 1:10 in fresh medium containing 25 $\mu$g/ml Ampicillin, incubated for two hours at 37EC and then induced with 1 mM IPTG for an additional 3 hours at 37EC. The cells were pelleted, resuspended in PBS and then exposed 3X to freezing on dry ice and thawing in a 65EC water bath alternately followed by sonication. The sonicated $E.$ $coli$ was then lysed by a solution containing 1% Triton X-100, 1% Tween 20 and 10 mM dithiothreitol (DTT) (Sigma Chemical Co., St. Louis, Mo.) and centrifuged at 10,000×g for 15 minutes at 4EC; the supernatant fluid was mixed with previously swollen glutathione agarose beads (Sigma Chemical Co., St. Louis, Mo.) for one hour at room temperature. The beads were collected by centrifugation at 500×g for 5 minutes and washed three times with PBS/1% Triton X-100. The fusion protein was eluted by competition with free glutathione in 50 mM Tris-HCl (pH 8.0) containing 5 mM reduced glutathione.

Detection of Antibodies to Recombinant Mitochondrial Antigen by ELISA

ELISA was performed to confirm the specific reactivity of PBC sera to recombinant fusion protein expressed from pML-MIT3 hybrid clones as well as PDC-E2 (414 bp) clone. The purified recombinant fusion protein of PDC-E2 (414 bp) and pML-MIT3 were coated onto microliter plates at 2: µg/ml for PDC-E2 (414 bp) and 4 µg/ml for pML-MIT3 overnight at 4EC. After washing 3 times in PBS/0.05% Tween the plates were blocked with 1% bovine serum albumin (BSA) in PBS for 1 hour. The plates were washed as above, incubated with 100 µl of sera (1:1000 dilution) for 1 hour at room temperature and then washed with PBS/ tween as above. Then 100 µl of horseradish-peroxidase-conjugated anti-human immunoglobulin (1:3000 dilution) (Tago, Burlingame, Calif.) was added to each well, incubated for 1 hour at room temperature and washed as above. Immunoreactivity was detected by measuring the optical density at 405 µm after incubating for 10 minutes with 100 µl of 40.0 mM 2,2'-azinobis (3-ethylbenzthiazoline sulfonic acid) containing 0.05 mol/L hydrogen peroxide in citrate buffer as substrate as described (Leung P S C, et al., Hepatology 1995;22:505–513). Optical density values greater than 2 standard deviation above the mean for normal control sera were regarded as positive.

Expression of Hybrid Clones

A PDC-E2 expressing clone (PDC-E2 (414 bp)) was shown to contain a 414 bp fragment of the human PDC-E2 cDNA by plasmid analysis and colony hybridization. SDS-PAGE analysis of the IPTG induced lysate of E. coli PDC-E2 (414 bp) demonstrated a recombinant polypeptide of 45 kD fused to glutathione-S-transferase (FIG. 2). The hybrid clone, pML-MIT2, contained a cDNA insert of a 414 bp fragment of the human PDC-E2 and a 354 bp fragment of the bovine BCOADC-E2 by agarose gel electrophoresis of EcoRI and BamHI digested PML-MIT2 plasmid DNA. SDS-PAGE analysis of the IPTG induced lysate of pML-MIT2 showed a recombinant fusion protein of 60 kD (FIG. 2). Analysis of pML-MIT3 crude lysate by SDS-PAGE confirmed the presence of a recombinant fusion protein with a molecular weight of 72 kD. Recombinant fusion proteins of PDC-E2 (414 bp), pML-MIT2 and pML-MIT3 reacted with PBC patient sera at 45 kD, 60 kD and 72 kD respectively (FIG. 2).

Three sera from different PBC patients were used to confirm the presence of three distinct immunoreactive epitopes expressed by hybrid clone pML-MIT3 and two distinct immunoreactive epitopes expressed by pML-MIT2 (FIG. 2). A PBC patient serum which was shown to be reactive with the 74 kD PDC-E2 mitochondrial antigen when probed against beef heart mitochondrial preparation reacted with all three recombinant fusion proteins of PDC-E2 (414 bp), pML-MIT2 and pML-MIT3. A PBC patient serum reactive only with the 52 kD BCOADC-E2 mitochondrial protein reacted with hybrid molecules of pML-MIT2 and pML-MIT3, but not with the PDC-E2 (414 bp) clone. Finally, a PBC patient serum containing only the 48 kD OGDC-E2 specific AMA reacted with the pML-MIT3 hybrid molecule alone, but not with PDC-E2 (414 bp) or pML-MIT2.

Specificity of the pML-MIT3 Hybrid Clone

PBC sera that had been preabsorbed with the IPTG induced lysate of transformed with pML-MIT3 were probed against recombinant PDC-E2, BCOADC-E2 and OGDC-E2 fusion proteins as well as beef heart mitochondrial protein (FIG. 3). Reactivity of PBC sera against recombinant PDC-E2, BCOADC-E2 and OGDC-E2 were completely removed after absorption. The reactivities of PBC sera with the 74 kD PDC-E2, 52 kD BCOADC-E2 and 48 kD OGDC-E2 antigens in beef heart mitochondria were also completely removed after absorption with pML-MIT3 recombinant fusion protein (FIG. 3). PBC sera that had been preabsorbed with the lysate of pGEX4T-1, a control clone, retained their reactivities against the 74 kD, 52 kD and 48 kD proteins in beef heart mitochondria and against the recombinant fusion proteins of PDC-E2, BCOADC-E2 and OGDC-E2. These data show that the recombinant fusion protein expressed from the pML-MIT3 hybrid clone contains all the epitopes to PDC-E2, BCOADC-E2 and OGDC-E2 recognized by autoantibodies from PBC patients.

Reactivity of PBC Sera Against Hybrid Molecules Expressed from PDC-E2 (414 bp), pML-MIT2 and pML-MIT3 in Immunoblotting Sera from patients with PBC, PSC, CAH, SLE and normal subjects were tested at 1:1,000 sera dilution for reactivity to the fusion proteins expressed from PDC-E2 (414 bp), pML-MIT2 and pML-MIT3 clones (Table 1). The PDC-E2 (414 bp), pML-MIT2 and pML-MIT3 recombinant fusion proteins migrate at approximately 45 kD, 60 kD and 72 kD respectively as described above. Out of 186 sera from patients with PBC 152 sera (81.7%) reacted with the 45 kD recombinant fusion protein of PDC-E2 (414 bp) clone. Among 34 PBC patients' sera that were not reactive with the PDC-E2 (414 bp) clone, 18 additional sera showed positive reactivity against the 60 kD recombinant fusion protein of pML-MIT2 clone, leading to an increase in frequency of AMA reactivity in PBC from 81.7% to 91.4%. Furthermore, when probed against the 72 kD

TABLE 2

AMA reactivity of PBC patients against 2-OADC subunits.[1]

| Antigen | positive/total (%) |
| --- | --- |
| PDC-E2 | 152/186 (81.7) |
| BCOADC-E2 | 110/186 (59.1) |
| OGDC-E2 | 51/186 (27.4) |
| PDC-E1"[2] | 49/186 (26.3) |
| PDC-E2 only | 36/168 (19.4) |
| BCOADC-E2 only | 13/186 (7.0) |
| OGDC-E2 only | 1/186 (0.5) |
| PDC-E1" only | 0/186 (0) |
| BCOADC-E2 and OGDC-E2 only | 4/186 (2.2) |
| BCOADC-E2 and PDC-E1" only | 1/186 (0.5) |
| pML-MIT2 | 170/186 (91.4) |
| pML-MIT3 | 171/186 (91.9)[3] |
| Nonreactive | 15/186 (8.1) |

[1].Sera reactivities against recombinant proteins were tested by immunoblotting as described in Materials and Methods.
[2].Antibody to PDC-E1" was determined by immunoblotting using beef heart mitochondrial preparation as antigen.
[3].Incidence of AMA positive sera is highest when pML-MIT3 was used as antigen.

pML-MIT3 recombinant fusion protein, 171/186 (91.9%) PBC patients' sera showed positive reactivity. On the other hand, no sera from patients with PSC (n=20), CAH (n=15) or SLE (n=20) contained autoantibodies to PDC-E2 (414 bp), pML-MIT2 or pML-MIT3 fusion protein, nor did the sera from normal subjects (n=20).

Characterization of AMA Reactivities in PBC

Sera from 186 patients with PBC were tested by immunoblotting for reactivity against the recombinant fusion proteins of PDC-E2 (414 bp), BCOADC-E2 (118 bp), OGDC-E2 (243 bp), pML-MIT2 and pML-MIT3 clone respectively. PDC-E1" specific AMA were detected by immunoblotting using beef heart mitochondria as the antigen source. The incidence of positive reactivities to recombinant fusion proteins of PDC-E2 (414 bp), BCOADC-E2 (118 bp) and OGDC-E2 (243 bp) was 152/186 (81.7%), 110/186 (59.1%) and 51/186 (27.4%) respectively (Table 2). Forty nine of 186 (26.3%) PBC patients were positive for PDC-E1" by immunoblotting on beef heart mitochondria Among 186 PBC patients' sera, 36 (19.4%), 13 (7.0%) and 1 (0.5%) reacted only with PDC-E2 (414 bp), BCOADC-E2 (118 bp) or OGDC-E2 (243 bp), respectively. None of 186 sera from patients with PBC reacted exclusively with PDC-E1". Four of 186 (2.2%) samples reacted with both BCOADC-E2 (118 bp) and OGDC-E2 (243 bp) but not with PDC-E2 (414 bp), and 1 of 186 (0.5%) reacted with both BCOADC-E2 (118 bp) and PDC-E1" but not with PDC-E2 (414 bp). On the other hand, when probed against hybrid molecules of pML-MIT2, 170 of 186 (91.4%) samples showed positive reactivity. In addition, the incidence of positive AMA reactivity in sera from patients with PBC increased to 171/186 (91.9%) when the pML-MIT3 hybrid molecule was used as the antigen. Finally we note that 15 (8.1 %) of the sera were negative for AMA either by immunofluorescence microscopy (at 1:80 sera dilution) or by immunoblotting (at 1,000 sera dilution) against the hybrid molecule (Table 2).

TABLE 1

Specificity of the antibodies against recombinant fusion proteins expressed from PDC-E2, pML-MIT2 and pML-MIT3 clones[1,2]

| | | No. positive/total (%) | | |
|---|---|---|---|---|
| Sera | Dilution | PDC-E2 (45 kD) | pML-MIT2 (60 kD) | pML-MIT3 (72 kD) |
| PBC[3] | 1:1000 | 152/186 (81.7) | 170/186 (91.4) | 171/186 (91.9) |
| PSC | 1:500 | 0/20 (0) | 0/20 (0) | 0/20 (0) |
| CAH | 1:500 | 0/15 (0) | 0/15 (0) | 0/15 (0) |
| SLE | 1:500 | 0/20 (0) | 0/20 (0) | 0/20 (0) |
| Healthy volunteers | 1:500 | 0/20 (0 | 0/20 (0) | 0/20 (0) |

[1] Sera reactivities against recombinant fusion proteins were tested at 1,1000 sera dilution by immunoblotting as described in "Materials and Methods".
[2] Reactivity after 12 to 14 hour autoradiographic exposure.
[3] Significantly higher than values for all other control groups by Student t test, $p < 0.001$.

Detection by ELISA Using Hybrid Molecule Expressed from pML-MIT3 Clone

One hundred and eighty six PBC patients' sera and 135 control sera were tested by ELISA for reactivity at 1,000 sera dilution to recombinant fusion protein expressed from pML-MIT3. This reactivity was compared with reactivity to PDC-E2 (414 bp) recombinant fusion protein. One hundred and forty eight of 186 (79.6%) sera from patients with PBC reacted to the recombinant PDC-E2 (414 bp) fusion protein by ELISA. In contrast, 171 of 186 (91.9%) sera from patients with PBC reacted with the hybrid molecule, pML-MIT3. Those PBC patients' sera that reacted with the hybrid molecule but not with PDC-E2 (414 bp) were found to contain autoantibodies to either BCOADC-E2 (13/186; 7%) or OGDC-E2 (1/186; 0.5%) by immunoblotting. Sera from none of the 135 disease control patients or normal volunteers showed significant reactivities against PDC-E2 or the hybrid molecule whereas sera reactivities from patients with PBC against the recombinant PDC-E2 414 fusion protein as well as the hybrid molecule of pML-MIT3 clone were significantly higher than in sera from patients with PSC, CAH, SLE and normal volunteers ($p<0.001$) (Table 3).

To further examine the sensitivity of the hybrid molecule as the antigen source, sera from 25 patients with PBC and 9 normal control were serially diluted from $10^{-3}$ to $10^{-5}$ and tested by ELISA for the reactivity to recombinant fusion proteins expressed from PDC-E2 414 and pML-MIT3 clones (Table 4). Only sera from PBC patients reacted to PDC-E2 414 and pML-MIT3. The control sera did not react. Furthermore, the reactivity of PBC sera to pML-MIT3 was higher than PDC-E2 414 even at $10^{-5}$ sera dilution.

The above specification, examples and data provide a complete description of the manufacture and use of the composition of the invention. Since many embodiments of the invention can be made without departing from the spirit and scope of the invention, the invention resides in the claims hereinafter appended.

TABLE 3

Specificity of Recombinant Designer Molecule[1]

| Recombinant Protein | PBC (n = 186) | PSC (n = 22) | CAH (n = 15) | SLE (n = 34) | Healthy volunteers (n = 64) |
|---|---|---|---|---|---|
| PDC-E2 414 | 0.384"0.025* (0.002–1.32) | 0.025"0.002 (0.007–0.047) | 0.030"0.005 (0.005–0.056) | 0.023"0.002 (0.002–0.0054) | 0.020"0.002 (0.001–0.045) |
| pML-MIT3 | 0.703"0.032* (0.001–2.15) | 0.033"0.002 (0.013–0.054) | 0.027"0.005 (0.004–0.054) | 0.034"0.001 (0.022–0.048) | 0.022"0.002 (0.001–0.045) |

[1] Sera relativities against recombinant fusion proteins were tested at 1,1000 sera dilution by ELISA as described in "Materials and Methods". The range in optical density at 405 μm are shown in parenthesis.
*Significantly higher than values for control group by Student t test ($p < 0.001$).

TABLE 4

Reactivity of sera from patients with PBC against recombinant PDC-E2 414 and pML-MIT3 by ELISA[1].

| Recombinant Protein | Group | $10^3$ | Sera 2.5 × $10^3$ | dilution $10^4$ | $10^5$ |
|---|---|---|---|---|---|
| PDC-E2 414 | PBC (n = 25) | 0.294"0.040[2]* (0.003–0.644)[3] | 0.225"0.034* (0.001–0.055) | 0.124"0.023* (0.00–0.41) | 0.037"0.008* (0.00–0.16) |
|  | Normal control (n = 9) | 0.013"0.002 (0.005–0.025) | 0.006"0.001 (0.001–0.012) | −0.002"0.002 (−0.01–0.003) | −0.006"0.03 (−0.02–0.003) |
| pML-MIT3 | PBC (n = 25) | 0.644"0.050* (0.191–1.17) | 0.465"0.051* (0.069–0.956) | 0.290"0.042* (0.028–0.804) | 0.085"0.017* (0.007–0.345) |
|  | Normal control (n = 9) | 0.018"0.003 (0.006–0.032) | 0.006"0.001 (0.002–0.012) | 0.007"0.007 (−0.01–0.06) | −0.004"0.003 (−0.02–0.005) |

[1]Sera reactivities against recombinant fusion proteins expressed from PDC-E2 414 and pML-MIT3 clones were tested by ELISA as described in "Materials and Methods".
[2]Mean " SEM.
[3]Range in optical density at 405 μm.
*Significantly higher than values for control group by Student t test ($p < 0.001$).

What is claimed is:

1. A recombinant fusion protein consisting of the PDC-E2, BCOADC-E2, and OGDC-E2 subunits or consisting of a fragment of each of said subunits comprising a lipoic acid binding domain, wherein said fusion protein is record by antibodies to each of the three lipoic acid binding domains.

2. The fusion protein of claim 1, wherein the portion of the lipoic acid binding domain of PDC comprises an amino acid sequence beginning with lysine at amino acid position 1 to leucine at amino acid position 138 of SEQ ID NO 2.

3. A fusion protein of claim 1, wherein the portion of the lipoic acid binding domain of BCOADC has an amino acid sequence beginning with glycine at amino acid position 1 to arginine at amino acid position 118 of SEQ ID NO 1.

4. The fusion protein of claim 1, wherein the portion of the lipoic acid binding domain of OGDC has an amino acid sequence beginning with asparagine at amino acid position 1 to alanine at amino acid position 82 SEQ ID NO 3.

5. The fusion protein of claim 1, having the amino acid sequence shown in FIG. 4.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 118 amino acids
      (B) TYPE: amino acid
      (C) STRANDEDNESS: single
      (D) TOPOLOGY: linear (ii) MOLECULE TYPE: protein (v) FRAGMENT TYPE: N-terminal (xi) SEQUENCE DESCRIPTION: SEQ ID NO:1:

```
Gly Gln Ile Val Gln Phe Lys Leu Ser Asp Ile Gly Glu Gly Ile Arg
 1               5                  10                  15

Glu Val Thr Val Lys Glu Trp Tyr Val Lys Glu Gly Asp Thr Val Ser
            20                  25                  30

Gln Phe Asp Ser Ile Cys Glu Val Glu Ser Asp Lys Ala Ser Val Thr
        35                  40                  45

Ile Thr Ser Arg Tyr Asp Gly Val Ile Lys Lys Leu Tyr Tyr Asn Leu
    50                  55                  60

Asp Asp Thr Ala Tyr Val Gly Lys Pro Leu Val Asp Ile Glu Thr Glu
65                  70                  75                  80

Ala Leu Lys Asp Ser Glu Glu Asp Val Val Glu Thr Pro Ala Val Ser
                85                  90                  95

His Asp Glu His Thr His Gln Glu Ile Leu Gly Gln Lys Thr Leu Gly
            100                 105                 110

Thr Pro Ala Val Arg Arg
        115
```

(2) INFORMATION FOR SEQ ID NO:2:

(i) SEQUENCE CHARACTERISTICS:
      (A) LENGTH: 118 amino acids
      (B) TYPE: amino acid
      (C) STRANDEDNESS: single
      (D) TOPOLOGY: linear (ii) MOLECULE TYPE: protein (v) FRAGMENT TYPE: N-terminal (xi) SEQUENCE DESCRIPTION: SEQ ID NO:2:

```
Gly Gln Ile Val Gln Phe Lys Leu Ser Asp Ile Gly Glu Gly Ile Arg
 1               5                  10                  15

Gln Val Thr Val Lys Glu Trp Tyr Val Lys Glu Gly Asp Thr Val Ser
                20                  25                  30

Gln Phe Asp Ser Ile Cys Glu Val Glu Ser Asp Lys Ala Ser Val Thr
            35                  40                  45

Ile Thr Ser Arg Tyr Asp Gly Val Ile Lys Lys Leu Tyr Tyr Asn Leu
        50                  55                  60

Asp Asp Thr Ala Tyr Val Gly Lys Pro Leu Val Asp Ile Glu Thr Glu
65                  70                  75                  80

Ala Leu Lys Asp Ser Glu Glu Asp Val Val Glu Thr Pro Ala Val Ser
                85                  90                  95

His Asp Glu His Thr His Gln Glu Ile Leu Gly Gln Lys Thr Leu Gly
                100                 105                 110

Ile Pro Ala Val Arg Arg
            115
```

(2) INFORMATION FOR SEQ ID NO:3:

(i) SEQUENCE CHARACTERISTICS:
      (A) LENGTH: 82 amino acids
      (B) TYPE: amino acid
      (C) STRANDEDNESS: single
      (D) TOPOLOGY: linear (ii) MOLECULE TYPE: protein (v) FRAGMENT TYPE: N-terminal (xi) SEQUENCE DESCRIPTION: SEQ ID NO:3:

```
Asn Asp Val Ile Thr Val Gln Thr Pro Ala Phe Ala Glu Ser Val Thr
 1               5                  10                  15

Glu Gly Asp Val Arg Trp Glu Lys Ala Val Gly Asp Ala Val Ala Glu
                20                  25                  30

Asp Glu Val Val Cys Glu Ile Glu Thr Asp Lys Thr Ser Val Gln Val
            35                  40                  45

Pro Ser Pro Ala Asn Gly Ile Ile Glu Ala Leu Leu Val Pro Asp Gly
        50                  55                  60

Gly Lys Val Glu Gly Gly Thr Pro Leu Pro Thr Leu Arg Lys Thr Gly
65                  70                  75                  80

Ala Ala
```

(2) INFORMATION FOR SEQ ID NO:4:

(i) SEQUENCE CHARACTERISTICS:
      (A) LENGTH: 363 amino acids
      (B) TYPE: amino acid
      (C) STRANDEDNESS: single
      (D) TOPOLOGY: linear (ii) MOLECULE TYPE: protein (v) FRAGMENT TYPE: N-terminal (xi) SEQUENCE DESCRIPTION: SEQ ID NO:4:

Leu Val Pro Arg Gly Ser Gly Gln Ile Val Gln Phe Lys Leu Ser Asp

```
         1               5                   10                  15
       Ile Gly Glu Gly Ile Arg Glu Val Thr Val Leu Glu Trp Tyr Val Lys
                         20                  25                  30

Glu Gly Asp Thr Val Ser Gln Phe Asp Ser Ile Cys Glu Val Gln Ser
                    35                  40                  45

Asp Lys Ala Ser Val Thr Ile Thr Ser Arg Tyr Asp Gly Val Ile Lys
                50                  55                  60

Lys Leu Tyr Tyr Asn Leu Asp Asp Thr Ala Tyr Val Gly Lys Pro Leu
        65                  70                  75                  80

Val Asp Ile Glu Thr Glu Ala Leu Lys Asp Ser Glu Glu Asp Val Val
                        85                  90                  95

Glu Thr Pro Ala Val Ser His Asp Glu His Thr His Gln Glu Ile Lys
                   100                 105                 110

Gly Gln Leu Thr Leu Gly Thr Pro Ala Val Arg Arg Gly Ser Pro Glu
                   115                 120                 125

Phe Lys Asn Tyr Thr Leu Asp Ser Ser Ala Ala Pro Thr Pro Gln Ala
           130                 135                 140

Ala Pro Ala Pro Thr Pro Ala Ala Thr Ala Ser Pro Pro Thr Pro Ser
       145                 150                 155                 160

Ala Gln Ala Pro Gly Ser Ser Tyr Pro Pro His Met Gln Val Leu Leu
                       165                 170                 175

Pro Ala Leu Ser Pro Thr Met Thr Met Gly Val Gln Arg Trp Glu Lys
                   180                 185                 190

Lys Val Gly Glu Lys Leu Ser Glu Gly Asp Leu Leu Ala Glu Ile Glu
                   195                 200                 205

Ile Asp Lys Ala Thr Ile Gly Phe Glu Val Gln Glu Glu Gly Tyr Leu
           210                 215                 220

Ala Lys Ile Leu Val Pro Glu Gly Thr Arg Asp Val Pro Leu Gly Thr
       225                 230                 235                 240

Pro Leu Cys Ile Ile Val Glu Lys Glu Ala Asp Ile Ser Ala Phe Ala
                       245                 250                 255

Asp Tyr Arg Pro Thr Glu Val Thr Asp Leu Glu Phe Pro Gly Arg Leu
                   260                 265                 270

Glu Ala Pro Gln Asn Asp Val Ile Thr Thr Val Gln Thr Pro Ala Phe
                   275                 280                 285

Ala Glu Ser Val Thr Glu Gly Asp Val Arg Trp Glu Lys Ala Val Gly
           290                 295                 300

Asp Ala Val Ala Glu Asp Glu Val Val Cys Glu Ile Glu Thr Asp Lys
       305                 310                 315                 320

Thr Ser Val Gln Val Pro Ser Pro Ala Asp Gly Ile Ile Glu Ala Leu
                       325                 330                 335

Leu Val Pro Asp Gly Gly Lys Val Glu Lys Lys Thr Pro Leu Phe Thr
                   340                 345                 350

Leu Arg Lys Thr Gly Ala Ala Arg Pro Ala Ser
                   355                 360

(2) INFORMATION FOR SEQ ID NO:5:

(i) SEQUENCE CHARACTERISTICS:
            (A) LENGTH: 1096 base pairs
            (B) TYPE: nucleic acid
            (C) STRANDEDNESS: single
            (D) TOPOLOGY: linear (ii) MOLECULE TYPE: cDNA
```

(xi) SEQUENCE DESCRIPTION: SEQ ID NO:5:

| | | | | | |
|---|---|---|---|---|---|
| CTGGTTCCGC | GTGGATCCGG | ACAGATTGTT | CAGTTCAAAC | TCTCAGACAT | TGGAGAAGGT | 60
| ATTAGAGAAG | TAACTGTTAA | AGAATGGTAT | GTAAAAGAAG | GAGATACAGT | GTCTCAGTTT | 120
| GATAGCATCT | GTGAAGTTCA | AAGTGATAAA | GCTTCTGTTA | CTATCACTAG | TCGTTATGAT | 180
| GGAGTCATTA | AAAAACTGTA | TTATAATCTA | GATGATACTG | CCTATGTGGG | AAAGCCATTA | 240
| GTAGACATAG | AAACGGAAGC | TTTAAAAGAT | TCAGAAGAAG | ATGTTGTTGA | AACCCCTGCT | 300
| GTGTCCCATG | ATGAACACAC | ACACCAAGAG | ATAAAGGGCC | AGAAAACACT | GGGCACTCCT | 360
| GCAGTTCGTC | GCGGATCCCC | GGAATTCAAA | AATTATACAC | TGGATTCCTC | AGCAGCACCT | 420
| ACCCCACAAG | CGGCCCCAGC | ACCAACCCCT | GCTGCCACTG | CTTCGCCACC | TACACCTTCT | 480
| GCTCAGGCTC | CTGGTAGCTC | ATATCCCCCT | CACATGCAGG | TACTTCTTCC | TGCCCTCTCT | 540
| CCCACCATGA | CCATGGGCAC | AGTTCAGAGA | TGGGAAAAAA | AAGTGGGTGA | GAAGCTAAGT | 600
| GAAGGAGACT | TACTGGCAGA | GATAGAAACT | GACAAAGCCA | CTATAGGTTT | TGAAGTACAG | 660
| GAAGAAGGTT | ATCTGGCAAA | AATCCTGGTC | CCTGAAGGCA | CAAGAGATGT | CCCTCTAGGA | 720
| ACCCCACTCT | GTATCATTGT | AGAAAAAGAG | GCAGATATAT | CAGCATTTGC | TGACTATAGG | 780
| CCAACCGAAG | TAACAGATTT | AGAATTCCCG | GGTCGACTCG | AGCGGCCGCA | GAATGATGTG | 840
| ATTACAGTCC | AGACCCCAGC | GTTTGCAGAG | TCTGTCACAG | AGGGAGATGT | CAGGTGGGAG | 900
| AAAGCTGTTG | GAGATGCAGT | TGCAGAAGAT | GAAGTGGTGT | GTGAGATTGA | GACAGACAAG | 960
| ACTTCTGTGC | AGGTTCCATC | ACCAGCAAAT | GGCATCATTG | AAGCTCTTTT | GGTACCCGAT | 1020
| GGGGGCAAAG | TTGAAGGAGG | AACTCCTCTA | TTCACACTCA | GGAAAACCGG | TGCTGCGCGG | 1080
| CCGGCATCGT | GACTGA | | | | | 1096

(2) INFORMATION FOR SEQ ID NO:6:

(i) SEQUENCE CHARACTERISTICS:
        (A) LENGTH: 263 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

| | | | | | |
|---|---|---|---|---|---|
| GCGGCCGCAG | AATGATGTGA | TTACAGTCCA | GACCCCAGCG | TTTGCAGAGT | CTGTCACAGA | 60
| GGGAGATGTC | AGGTGGGAGA | AAGCTGTTGG | AGATGCAGTT | GCAGAAGATG | AAGTGGTGTG | 120
| TGAGATTGAG | ACAGACAAGA | CTTCTGTGCA | GGTTCCATCA | CCAGCAAATG | GCATCATTGA | 180
| AGCTCTTTTG | GTACCCGATG | GGGGCAAAGT | TGAAGGAGGA | ACTCCTCTAT | TCACACTCAG | 240
| GAAAACCGGT | GCTGCGCGGC | CGC | | | | 263

(2) INFORMATION FOR SEQ ID NO:7:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

| | | | | | |
|---|---|---|---|---|---|
| GGATCCGGAC | AGATTGTTCA | GTTCAAACTC | TCAGACATTG | GAGAAGGTAT | TAGAGAAGTA | 60
| ACTGTTAAAG | AATGGTATGT | AAAAGAAGGA | GATACAGTGT | CTCAGTTTGA | TAGCATCTGT | 120

```
GAAGTTCAAA GTGATAAAGC TTCTGTTACT ATCACTAGTC GTTATGATGG AGTCATTAAA      180

AAACTGTATT ATAATCTAGA TGATACTGCC TATGTGGGAA AGCCATTAGT AGACATAGAA      240

ACGGAAGCTT TAAAAGATTC AGAAGAAGAT GTTGTTGAAA CCCCTGCTGT GTCCCATGAT      300

GAACACACAC ACCAAGAGAT AAAGGGCCAG AAAACACTGG GCACTCCTGC AGTTCGTCGC      360

GGATCC                                                                366

(2) INFORMATION FOR SEQ ID NO:8:

(i) SEQUENCE CHARACTERISTICS:
          (A) LENGTH: 426 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:8:

GAATTCAAAA ATTATACACT GGATTCCTCA GCAGCACCTA CCCCACAAGC GGCCCCAGCA       60

CCAACCCCTG CTGCCACTGC TTCGCCACCT ACACCTTCTG CTCAGGCTCC TGGTAGCTCA      120

TATCCCCCTC ACATGCAGGT ACTTCTTCCT GCCCTCTCTC CCACCATGAC CATGGGCACA      180

GTTCAGAGAT GGGAAAAAAA AGTGGGTGAG AAGCTAAGTG AAGGAGACTT ACTGGCAGAG      240

ATAGAAACTG ACAAAGCCAC TATAGGTTTT GAAGTACAGG AAGAAGGTTA TCTGGCAAAA      300

ATCCTGGTCC CTGAAGGCAC AAGAGATGTC CCTCTAGGAA CCCCACTCTG TATCATTGTA      360

GAAAAAGAGG CAGATATATC AGCATTTGCT GACTATAGGC AACCGAAGT AACAGATTTA      420

GAATTC                                                                426

(2) INFORMATION FOR SEQ ID NO:9:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:9:

GGAATTCAAA AATTATACAC TG                                               22

(2) INFORMATION FOR SEQ ID NO:10:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:10:

GGAATTCTAA ATCTGTTACT TC                                               22

(2) INFORMATION FOR SEQ ID NO:11:

(i) SEQUENCE CHARACTERISTICS:
          (A) LENGTH: 27 base pairs
          (B) TYPE: nucleic acid
          (C) STRANDEDNESS: single
          (D) TOPOLOGY: linear
```

```
        (ii) MOLECULE TYPE: cDNA (xi) SEQUENCE DESCRIPTION: SEQ ID NO:11:

CGCGGATCCG GACAGATTGT TCAGTTC                                         27

(2) INFORMATION FOR SEQ ID NO:12:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

CGCGGATCCG CGACGAACTG CAGGAGT                                         27

(2) INFORMATION FOR SEQ ID NO:13:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

AAGGAAAAAA GCGGCCGCAT AATGATGTGA TTAC                                 34

(2) INFORMATION FOR SEQ ID NO:14:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

AAGGAAAAAA GCGGCCGCTC AGCACCGGTT TTCC                                 34
```